United States Patent
Hungenberg et al.

(10) Patent No.: US 9,125,417 B2
(45) Date of Patent: *Sep. 8, 2015

(54) PESTICIDE COMPOSITION COMPRISING FOSETYL-ALUMINIUM, PROPAMOCARB-HCL AND AN INSECTICIDE ACTIVE SUBSTANCE

(71) Applicant: BAYER CROPSCIENCE AG, Monheim (DE)

(72) Inventors: Heike Hungenberg, Langenfeld (DE); Wolfgang Thielert, Odenthal (DE); Koen Van Den Eynde, Merchtem (BE)

(73) Assignee: BAYER INTELLECTUAL PROPERTY GMBH, Monheim (DE)

( * ) Notice: Subject to any disclaimer, the term of this patent is extended or adjusted under 35 U.S.C. 154(b) by 243 days.

This patent is subject to a terminal disclaimer.

(21) Appl. No.: 13/781,228

(22) Filed: Feb. 28, 2013

(65) Prior Publication Data

US 2013/0178447 A1 Jul. 11, 2013

Related U.S. Application Data

(62) Division of application No. 12/520,565, filed as application No. PCT/EP2007/006430 on Dec. 21, 2007.

(30) Foreign Application Priority Data

Dec. 22, 2006 (EP) ..................................... 06127178

(51) Int. Cl.
*A01N 57/12* (2006.01)
*A01N 47/12* (2006.01)

(52) U.S. Cl.
CPC ................ *A01N 57/12* (2013.01); *A01N 47/12* (2013.01)

(58) Field of Classification Search
CPC .............................. A01N 57/12; A01N 47/12
See application file for complete search history.

(56) References Cited

U.S. PATENT DOCUMENTS

| 6,358,938 B1 | 3/2002 | Donnadieu et al. |
| 6,603,044 B1 | 8/2003 | Tohnishi et al. |
| 2008/0051457 A1 | 2/2008 | Nakao et al. |

FOREIGN PATENT DOCUMENTS

| GB | 1212708 A | 11/1970 |
| GB | 1449394 A | 9/1976 |
| WO | 9942468 A1 | 8/1999 |
| WO | 2004080181 A1 | 9/2004 |
| WO | 2006024333 A2 | 3/2006 |

OTHER PUBLICATIONS

Colby, "Calculating Synergistic and Antagonistic Responses of Herbicide Combinations," Weeds, (1967), 15, pp. 20-22.
International Search Report for PCT/EP2007/064430, Dated Mar. 11, 2009 (4 pages).

*Primary Examiner* — Trevor Love
(74) *Attorney, Agent, or Firm* — Miles & Stockbridge P.C.

(57) ABSTRACT

The present invention relates to a pesticide composition intended for protecting plants, crops or seeds against phytopathogenic fungi or damaging insects, and the corresponding methods of treatment using the said composition. More precisely, the subject of the present invention is a pesticide composition based on fosetyl-Al, propamocarb-HCl, an insecticide active substance and optionally a further fungicide active substance.

13 Claims, No Drawings

PESTICIDE COMPOSITION COMPRISING FOSETYL-ALUMINIUM, PROPAMOCARB-HCL AND AN INSECTICIDE ACTIVE SUBSTANCE

CROSS REFERENCE TO RELATED APPLICATIONS

This application is a Divisional application of U.S. application Ser. No. 12/520,565, filed Jun. 22, 2009, which is a U.S. National Phase Application of International Application Number PCT/EP2007/064430, filed Dec. 21, 2007, which claims the priority of European Application No. 06127178.9, filed Dec. 22, 2006, the contents of all of which are incorporated herein by reference in their entireties.

BACKGROUND

1. Field of the Invention

The present invention relates to a pesticide composition intended for protecting plants, crops or seeds against fungal diseases or insect damages, and the corresponding methods of protection by application of the said composition. More precisely, the subject of the present invention is a pesticide composition based on fosetyl-Al, propamocarb-HCl and an insecticide active substance or compound and optionally a further fungicide active substance or compound.

2. Description of Related Art

As regards pesticide activity, in particular for the protection of crops, one of the problems at the heart of the research studies carried out in this technical field is the improvement of performances, in particular in terms of biological activity and in particular in terms of maintaining such an activity over time.

The present invention provides a pesticide composition which can be used, in particular by the farmer, for controlling the pest infesting crops and in particular for controlling insects or diseases of corn, beet, cotton, canola, beans, peanuts vegetables, lucerne, soybean, market garden crops, turf, wood, tree and horticultural plants, for example *Pythium* on corn.

The pesticide compounds useful for the protection of plants must be endowed with an ecotoxicity which is reduced to the minimum. As far as possible, they should not be dangerous or toxic to the operator during use. The economic factor should of course not be overlooked in the search for novel pesticide agents.

Fosetyl-aluminium or fosetyl-Al is a known compound having as chemical name aluminium ethylhydrogenphosphonate-fosetyl-Al is described in British patent GB-1449394—and which is represented by the following formula:

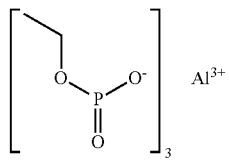

Propamocarb-hydrochloride or propamocarb-HCl is a known compound having as chemical name propyl[3-(dimethylamino)propyl]carbamate hydrochloride-propamocarb is described in British patent GB-1212708—and which is represented by the following formula:

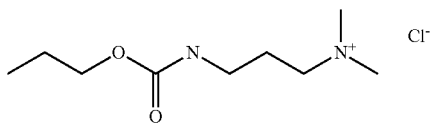

Mixture of fosetyl-Al and propamocarb is described in U.S. Pat. No. 6,358,938 wherein activity of such a mixture is reported on several plant diseases. This document is silent with regard to any results or biological activity of such potential mixtures. In particular, this document does not report any activity to specifically control seed diseases with a mixture of fosetyl-Al with propamocarb-HCl nor this document discloses any mixture of fosetyl-Al and propamocarb-HCl with any insecticide active substance.

In the same manner, in 1991, Couch and Smith described the use of various dose rates of fosetyl-Al and propamocarb mixtures to synergistically control turf diseases. In this article, there is no mention to any further use of an insecticide substance.

In international patent application WO-2006/024333 there are generically disclosed mixtures of certain neonicotinoid insecticide compounds with known fungicide substances; fosetyl-Al and propamocarb-HCl are part of long list of such known fungicide substances. However, there is no specific disclosure in this document of any combination comprising fosetyl-Al and propamocarb-HCl in mixture with an insecticide substance.

In international patent applications WO-2004/080181 there are generically disclosed numerous mixtures of some phtalamide insecticide compounds with known fungicide substances. The association of these insecticide compounds with fosetyl-Al and propamocarb-HCl has not been disclosed nor has been subject to any experimentation. Such an association does not form part of the present invention.

SUMMARY

In a main aspect, the present invention provides a composition comprising:
A) the compounds
A1) fosetyl-Al,
A2) propamocarb-HCl, in a A1/A2 weight ratio ranging from 1/12 to 12/1, and
B) an insecticide compound in an A/B weight ratio ranging from 1/1,000 to 1,000/1; provided that insecticide compound B differs from compounds of formula (I)

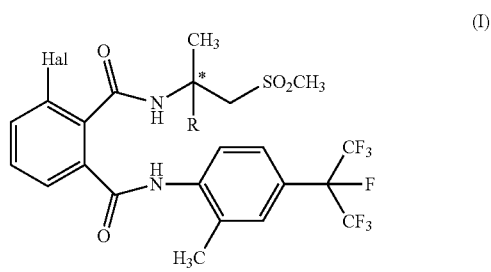

wherein:
Hal represents a chlorine atom, a bromine atom or a iodine atom;
R represents hydrogen or methyl and * may represent a carbon atom in R— or S— configuration.

For the various aspects of composition according to the invention as herein-described fosetyl-Al can be replaced by a phosphorous acid derivative such as metal phosphites like fosetyl-sodium, and phosphorous acid itself and its alkali metal or alkaline earth metal salts. In case of replacement, phosphorous acid itself is the preferred substitute of fosetyl-Al, any composition comprising phosphorous acid is part of the present invention.

According to the present invention, propamocarb-HCl and propamocarb can be used in the same manner. Both forms are part of the present invention in its various aspects or preferences.

The present invention advantageously provides a pesticide composition which is completely high-performing in particular as regards its efficacy against pests and the perenniallity of this efficacy so as to be able to reduce the doses of chemical products spread in the environment for combating pest damages or attacks of plants or crops.

The invention provides a pesticide composition capable to be more active and active for longer, and which therefore has a lower dose, but which is also less toxic, in particular in the treatment of plants and particularly the foliar and seed treatments of fungal diseases or the control of insects, for example, of cereals, cotton, peanut, bean, beet, canola, Solanaceae, grapevine, vegetables, lucerne, soybean, market garden crops, turf, wood or horticultural plants.

The composition according to the invention allows controlling a broad variety of insects or fungi. For example, the pesticide composition according to the invention exhibits an improved efficacy against fungus like Plasmodiophoromycetes, Oomycetes, Chytridiomycetes, Zygomycetes, Basidiomycetes, Deuteromycetes and Ascomycetes.

All these objectives or advantages, among others, were achieved by finding a pesticide composition comprising fosetyl-Al, propamocarb-HCl; an insecticide compound and optionally a further fungicide compound. Such a composition surprisingly and unexpectedly allows a very high and perennial insecticide or anti-fungal efficacy against a broad spectrum of insects or fungi and in particular against those responsible for diseases or damages of corn for example to Oomycetes. Other insect pests or diseases of corn can be controlled with the pesticide composition according to the invention, in particular the control of Ascomycetes or Basidiomycetes.

The pesticide composition according to the invention may also be used for the treatment of bacterial or virus diseases.

Insects or nematodes that can be controlled with the pesticide composition according to the invention include a broad variety of these damaging organisms.

DETAILED DESCRIPTION OF A PREFERRED EMBODIMENT

For the composition according to the invention, insecticide compound B is preferably selected in the list consisting of:

B1) a compound capable to act as an acetylcholine receptor agonist or antagonist, for example a compound of the type chloronicotinyl like acetamiprid, clothianidin, dinotefuran, imidacloprid, imidaclothiz also known as (2E)-1-[(2-chloro-1,3-thiazol-5-yl)methyl]-N-nitroimidazolidin-2-imine, nitenpyram, nithiazine, thiacloprid; thiamethoxam; nicotine, bensultap, cartap, (2E)-1-[(2-chloro-1,3-thiazol-5-yl)methyl]-3,5-dimethyl-N-nitro-1,3,5-triazinan-2-imine;

B2) a compound capable to inhibit acetylcholinesterase (ACHE), for example a compound of the type carbamate like alanycarb, aldicarb, aldoxycarb, allyxycarb, aminocarb, bendiocarb, benfuracarb, bufencarb, butacarb, butocarboxim, butoxycarboxim, carbaryl, carbofuran, carbosulfan, cloethocarb, dimetilan, ethiofencarb, fenobucarb, fenothiocarb, formetanate, furathiocarb, isoprocarb, metam-sodium, methiocarb, methomyl, metolcarb, oxamyl, pirimicarb, promecarb, propoxur, thiodicarb, thiofanox, trimethacarb, XMC, xylylcarb; triazamate; a compound of the type organophosphate like acephate, azamethiphos, azinphos (-methyl, -ethyl), bromophos-ethyl, bromfenvinfos (-methyl), butathiofos, cadusafos, carbopheno-thion, chlorethoxyfos, chlorfenvinphos, chlormephos, chlorpyrifos (-methyl/-ethyl), coumaphos, cyanofenphos, cyanophos, chlorfenvinphos, demeton-s-methyl, demeton-s-methylsulphon, dialifos, diazinon, dichlofenthion, dichlorvos/ddvp, dicrotophos, dimethoate, dimethylvinphos, dioxabenzofos, disulfoton, epn, ethion, ethoprophos, etrimfos, famphur, fenamiphos, fenitrothion, fensulfothion, fenthion, flupyrazofos, fonofos, formothion, fosmethilan, fosthiazate, heptenophos, iodofenphos, iprobenfos, isazofos, isofenphos, isopropyl o-salicylate, isoxathion, malathion, mecarbam, methacrifos, methamidophos, methidathion, mevinphos, monocrotophos, naled, omethoate, oxydemeton-methyl, parathion (-methyl/-ethyl), phenthoate, phorate, phosalone, phosmet, phosphamidon, phosphocarb, phoxim, pirimiphos (-methyl/-ethyl), profenofos, propaphos, propetamphos, prothiofos, prothoate, pyraclofos, pyridaphenthion, pyridathion, quinalphos, sebufos, sulfotep, sulprofos, tebupirimfos, temephos, terbufos, tetrachlorvinphos, thiometon, triazophos, triclorfon, vamidothion;

B3) a compound capable to modulate the sodium channel or to block the voltage dependant sodium channel, for example a compound of the type pyrethroid like acrinathrin, allethrin (d-cis-trans, d-trans), beta-cyfluthrin, bifenthrin, bioallethrin, bioallethrin-s-cyclopentyl-isomer, bioethanomethrin, biopermethrin, bioresmethrin, chlovaporthrin, cis-cypermethrin, cis-resmethrin, cis-permethrin, clocythrin, cycloprothrin, cyfluthrin, cyhalothrin, cypermethrin (alpha, beta-, theta-, zeta-), cyphenothrin, deltamethrin, empenthrin (1R-isomer), esfenvalerate, etofenprox, fenfluthrin, fenpropathrin, fenpyrithrin, fenvalerate, flubrocythrinate, flucythrinate, flufenprox, flumethrin, fluvalinate, fubfenprox, gamma-cyhalothrin, imiprothrin, kadethrin, lambda-cyhalothrin, metofluthrin, permethrin (cis-, trans-), phenothrin (1r-trans isomer), prallethrin, profluthrin, protrifenbute, pyresmethrin, resmethrin, RU15525, silafluofen, tau-fluvalinate, tefluthrin, terallethrin, tetramethrin (-1r-isomer), tralomethrin, transfluthrin, ZX18901, pyrethrins (pyrethrum); for example DDT; for example a compound of the type oxadiazine like indoxacarb;

B4) a compound capable to modulate acetylcholine receptor, for example a compound of the type spinosyn like spinosad;

B5) a compound capable to act as GABA-gated chloride channel antagonist, for example a compound of the type cyclodiene organochlorine like camphechlor, chlordane, endosulfan, gamma-HCH, HCH, heptachlor, lindane, methoxychlor; a compound of the type fiprole like acetoprole, ethiprole, fipronil, vaniliprole;

B6) a compound capable to activate the chloride channel, for example a compound of the type mectin like avermectin, emamectin, emamectin-benzoate, ivermectin, milbemycin;

B7) a compound capable to mimic a juvenile hormone like diofenolan, epofenonane, fenoxycarb, hydroprene, kinoprene, methoprene, pyriproxifen, triprene;

B8) a compound capable to act as an ecdysone agonist or disruptor, for example a compound of the type diacylhydrazine like chromafenozide, halofenozide, methoxyfenozide, tebufenozide;

B9) a compound capable to inhibit chitin biosynthesis, for example a compound of the type benzoylurea like bistrifluoron, chlofluazuron, diflubenzuron, fluazuron, flucycloxuron, flufenoxuron, hexaflumuron, lufenuron, novaluron, noviflumuron, penfluoron, teflubenzuron, triflumuron; buprofezin; cyromazine;

B10) a compound capable to inhibit oxidative phosphorylation or to disrupt ATP, like diafenthiuron; for example a compound of the type organotin like azocyclotin, cyhexatin, fenbutatin-oxide;

B11) a compound capable to uncouple oxidative phosphorylation via disruption of H proton gradient, for example a compound of the type pyrrole like chlorfenapyr; a compound of the type dinitrophenole like binapacyrl, dinobuton, dinocap, DNOC;

B12) a compound capable to inhibit site I electron transport, for example a compound of the type METI like fenazaquin, fenpyroximate, pyrimidifen, pyridaben, tebufenpyrad, tolfenpyrad; hydramethylnon; dicofol;

B13) a compound capable to inhibit site II electron transport like rotenone;

B14) a compound capable to inhibit site III electron transport like acequinocyl, fluacrypyrim;

B15) a compound capable to act as a microbial disruptor of insect midgut or intestinal membrane like stains of *Bacillus thuringiensis*;

B16) a compound capable to inhibit lipid synthesis, for example a compound of the type tetronic acid insecticide like spirodiclofen, spiromesifen or a compound of the type tetramic acid insecticide like spirotetramat also known as carbonic acid cis-3-(2,5-dimethylphenyl)-8-methoxy-2-oxo-1-azaspiro[4.5]dec-3-en-4-yl ethyl ester (CAS-reg-n° 203313-25-1) and 3-(2,5-dimethylphenyl)-8-methoxy-2-oxo-1-azaspiro[4.5]dec-3-en-4-yl ethyl carbonate also known as carbonic acid 3-(2,5-dimethylphenyl)-8-methoxy-2-oxo-1-azaspiro[4.5]dec-3-en-4-yl ethyl ester (CAS-reg-n° 382608-10-8);

B17) a compound of the type carboxamide like flonicamid;

B18) a compound capable to act as an octopaminergic agonist like amitraz;

B19) a compound capable to inhibit magnesium-stimulated ATP-ase like propargite;

B20) a compound of the type BDCA or capable to act as a ryanodin receptor agonist like rynaxypyr or phthalamides, e.g. flubendiamide also known as N2-[1,1-dimethyl-2-(methylsulfonyl)ethyl]-3-iodo-N-1-[2-methyl-4-[1,2,2,2-tetrafluoro-1-(trifluoromethyl)ethyl]phenyl]-1,2-benzenedicarboxamide (CAS-reg-n° 272451-65-7);

B21) a compound of the type nereistoxin analogue insecticide like thiocyclam hydrogen oxalate, thiosultap-sodium;

B22) a compound of the types biologica, hormones or pheromones like azadirachtin, *Bacillus* spec., *Beauveria* spec., codlemone, *Metarrhizium* spec., *Paecilomyces* spec., thuringiensin, *Verticillium* spec.;

B23) a compound of unknown or non-specific mode of action, for example a compound of the type fumigant like aluminium phosphide, methyl bromide, sulfuryl fluoride; a compound of the type selective feeding blocker like cryolite, flonicamid, pymetrozine; a compound of the type mite growth inhibitor like clofentezine, etoxazole, hexythiazox; amidoflumet, benclothiaz, benzoximate, bifenazate, bromopropylate, buprofezin, chinomethionat, chlordimeform, chlorobenzilate, chloropicrin, clothiazoben, cycloprene, cyflumetofen, dicyclanil, fenoxacrim, fentrifanil, flubendiamide, flubenzimine, flufenerim, flutenzin, gossyplure, hydramethylnone, japonilure, metoxadiazone, petroleum, piperonyl butoxide, potassium oleate, pyrafluprole, pyridalyl, pyriprole, sulfluramid, tetradifon, tetrasul, triarathene, verbutin.

More preferably, the composition according to the invention comprises fosetyl-Al, propamocarb-HCl and abamectin; fosetyl-Al, propamocarb-HCl and acephate; fosetyl-Al, propamocarb-HCl and acetamiprid; fosetyl-Al, propamocarb-HCl and acrinathrin; fosetyl-Al, propamocarb-HCl and aldicarb; fosetyl-Al, propamocarb-HCl and alpha-cypermethrin; fosetyl-Al, propamocarb-HCl and beta-cyfluthrin; fosetyl-Al, propamocarb-HCl and bifenthrin; fosetyl-Al, propamocarb-HCl and carbaryl; fosetyl-Al, propamocarb-HCl and carbofuran; fosetyl-Al, propamocarb-HCl and chlorfenapyr; fosetyl-Al, propamocarb-HCl and chlorfluazuron; fosetyl-Al, propamocarb-HCl and chlorpyrifos-E; fosetyl-Al, propamocarb-HCl and clothianidin; fosetyl-Al, propamocarb-HCl and cyfluthrin; fosetyl-Al, propamocarb-HCl and cypermethrin; fosetyl-Al, propamocarb-HCl and cyromazine; fosetyl-Al, propamocarb-HCl and deltamethrin; fosetyl-Al, propamocarb-HCl and diflubenzuron; fosetyl-Al, propamocarb-HCl and dinotefuran; fosetyl-Al, propamocarb-HCl and emamectin-benzoate; fosetyl-Al, propamocarb-HCl and ethiprole; fosetyl-Al, propamocarb-HCl and fenpyroximate; fosetyl-Al, propamocarb-HCl and fipronil; fosetyl-Al, propamocarb-HCl and flonicamid; fosetyl-Al, propamocarb-HCl and flubendiamide; fosetyl-Al, propamocarb-HCl and flufenoxuron; fosetyl-Al, propamocarb-HCl and gamma-cyhalothrin; fosetyl-Al, propamocarb-HCl and hexaflumuron; fosetyl-Al, propamocarb-HCl and imidacloprid; fosetyl-Al, propamocarb-HCl and indoxacarb; fosetyl-Al, propamocarb-HCl and L-cyhalothrin; fosetyl-Al, propamocarb-HCl and lepimectin; fosetyl-Al, propamocarb-HCl and lufenuron; fosetyl-Al, propamocarb-HCl and methamidophos; fosetyl-Al, propamocarb-HCl and methiocarb; fosetyl-Al, propamocarb-HCl and methomyl; fosetyl-Al, propamocarb-HCl and methoxyfenozide; fosetyl-Al, propamocarb-HCl and milbemycin; fosetyl-Al, propamocarb-HCl and nitenpyram; fosetyl-Al, propamocarb-HCl and novaluron; fosetyl-Al, propamocarb-HCl and profenofos; fosetyl-Al, propamocarb-HCl and pymetrozine; fosetyl-Al, propamocarb-HCl and rynaxapyr; fosetyl-Al, propamocarb-HCl and spinosad; fosetyl-Al, propamocarb-HCl and spirodiclofen; fosetyl-Al, propamocarb-HCl and spiromesifen; fosetyl-Al, propamocarb-HCl and spirotetramate; fosetyl-Al, propamocarb-HCl and tebufenozide; fosetyl-Al, propamocarb-HCl and tebufenozide; fosetyl-Al, propamocarb-HCl and tebufenpyrad; fosetyl-Al, propamocarb-HCl and tebufenpyrad; fosetyl-Al, propamocarb-HCl and tebupirimphos; fosetyl-Al, propamocarb-HCl and teflubenzuron; fosetyl-Al, propamocarb-HCl and tefluthrin; fosetyl-Al, propamocarb-HCl and thiacloprid; fosetyl-Al, propamocarb-HCl and thiamethoxam; fosetyl-Al, propamocarb-HCl and thiodicarb; fosetyl-Al, propamocarb-HCl and triazophos triflumuron; fosetyl-Al, propamocarb-HCl and imidaclothiz; fosetyl-Al, propamocarb-HCl and (2E)-1-[(2-chloro-1,3-thiazol-5-yl)methyl]-3,5-dimethyl-N-nitro-1,3,5-triazinan-2-imine.

Even more preferably, the composition according to the invention comprises fosetyl-Al, propamocarb-HCl and abamectin; fosetyl-Al, propamocarb-HCl and acetamiprid; fosetyl-Al, propamocarb-HCl and aldicarb; fosetyl-Al, propamocarb-HCl and beta-cyfluthrin; fosetyl-Al, propamocarb-HCl and carbofuran; fosetyl-Al, propamocarb-HCl and chlorpyrifos-E; fosetyl-Al, propamocarb-HCl and clothianidin; fosetyl-Al, propamocarb-HCl and cypermethrin; fosetyl-Al, propamocarb-HCl and cyromazine; fosetyl-Al, propamocarb-HCl and deltamethrin; fosetyl-Al, propamocarb-HCl and diflubenzuron; fosetyl-Al, propamocarb-HCl and emamectin-benzoate; fosetyl-Al, propamocarb-HCl and ethiprole; fosetyl-Al and fipronil; fosetyl-Al and gamma-cyhalothrin; fosetyl-Al, propamocarb-HCl and imidacloprid; fosetyl-Al, propamocarb-HCl and L-cyhalothrin; fosetyl-Al, propamocarb-HCl and lufenuron; fosetyl-Al, propamocarb-HCl and methiocarb; fosetyl-Al, propamocarb-HCl and methoxyfenozide; fosetyl-Al, propamocarb-HCl and pymetrozine; fosetyl-Al, propamocarb-HCl and rynaxapyr; fosetyl-Al, propamocarb-HCl and spinosad; fosetyl-Al, propamocarb-HCl and spirodiclofen; fosetyl-Al, propamocarb-HCl and spiromesifen; fosetyl-Al, propamocarb-HCl and spirotetramate; fosetyl-Al, propamocarb-HCl and tebufenozide; fosetyl-Al, propamocarb-HCl and tebufenpyrad; fosetyl-Al, propamocarb-HCl and tefluthrin; fosetyl-Al, propamocarb-HCl and thiacloprid; fosetyl-Al, propamocarb-HCl and thiamethoxam; fosetyl-Al, propamocarb-HCl and thiodicarb; fosetyl-Al, propamocarb-HCl and triflumuron; fosetyl-Al, propamocarb-HCl and imidaclothiz; preferred composition according to the invention comprises fosetyl-Al, propamocarb-HCl and (2E)-1-[(2-chloro-1,3-thiazol-5-yl)methyl]-3,5-dimethyl-N-nitro-1,3,5-triazinan-2-imine.

Still even more preferrably, the composition according to the invention comprises fosetyl-Al, propamocarb-HCl and abamectin; fosetyl-Al, propamocarb-HCl and aldicarb; fosetyl-Al, propamocarb-HCl and beta-cyfluthrin; fosetyl-Al, propamocarb-HCl and chlorpyrifos-E; fosetyl-Al, propamocarb-HCl and clothianidin; fosetyl-Al, propamocarb-HCl and cyromazine; fosetyl-Al, propamocarb-HCl and deltamethrin; fosetyl-Al, propamocarb-HCl and diflubenzuron; fosetyl-Al, propamocarb-HCl and emamectin-benzoate; fosetyl-Al, propamocarb-HCl and fipronil; fosetyl-Al, propamocarb-HCl and gamma-cyhalothrin; fosetyl-Al, propamocarb-HCl and imidacloprid; fosetyl-Al, propamocarb-HCl and L-cyhalothrin; fosetyl-Al, propamocarb-HCl and methiocarb; fosetyl-Al, propamocarb-HCl and pymetrozine; fosetyl-Al, propamocarb-HCl and rynaxapyr; fosetyl-Al, propamocarb-HCl and spinosad; fosetyl-Al, propamocarb-HCl and spirodiclofen; fosetyl-Al, propamocarb-HCl and spiromesifen; fosetyl-Al, propamocarb-HCl and spirotetramate; fosetyl-Al, propamocarb-HCl and tebufenozide; fosetyl-Al, propamocarb-HCl and tebufenpyrad; fosetyl-Al, propamocarb-HCl and tefluthrin; fosetyl-Al, propamocarb-HCl and thiamethoxam; fosetyl-Al, propamocarb-HCl and thiodicarb; fosetyl-Al, propamocarb-HCl and imidaclothiz; fosetyl-Al, propamocarb-HCl and (2E)-1-[(2-chloro-1,3-thiazol-5-yl)methyl]-3,5-dimethyl-N-nitro-1,3,5-triazinan-2-imine.

For the composition according to the invention the A1/A2 weight ratio preferably ranges from 1/3 to 3/1; more preferably is equal to 1.

For the composition according to the invention the A/B weight ratio preferably ranges from 1/125 to 125/1; more preferably from 1/25 to 25/1.

According to another aspect of the present invention, in the pesticide composition according to the invention, the compound ratio A/B can be advantageously selected so as to produce a synergistic effect. The term synergistic effect is understood to mean in particular that defined by Colby in an article entitled "Calculation of the synergistic and antagonistic responses of herbicide combinations" Weeds, (1967), 15, pages 20-22.

The latter article mentions the formula:

$$E = X + Y - \frac{XY}{100}$$

wherein E represents the expected percentage of inhibition of the pest for the combination of the two compounds at defined doses (for example equal to x and y respectively), X is the percentage of inhibition observed for the pest by compound A at a defined dose (equal to x), Y is the percentage of inhibition observed for the pest by compound B at a defined dose (equal to y). When the percentage of inhibition observed for the combination is greater than E, there is a synergistic effect.

The term "synergistic effect" also means the effect defined by application of the Tammes method, "Isoboles, a graphic representation of synergism in pesticides", Netherlands Journal of Plant Pathology, 70 (1964), pages 73-80.

In a further aspect, the present invention provides a composition comprising:
A) the compounds
 A1) fosetyl-Al,
 A2) propamocarb-HCl, in a A1/A2 weight ratio ranging from 1/12 to 12/1;
B) an insecticide compound and
C) a further fungicide compound in an A/B/C weight ratio ranging from 1/1,000/1,000 to 1/0.001/0.001; provided that insecticide compound B differs from compounds of formula (I)

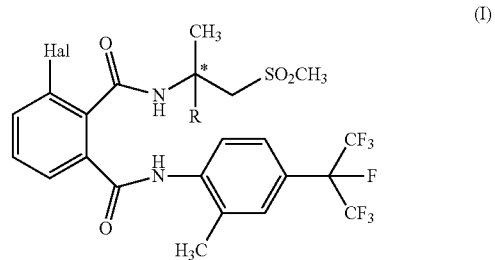

(I)

wherein:
 Hal represents a chlorine atom, a bromine atom or a iodine atom;
 R represents hydrogen or methyl and * may represent a carbon atom in R— or S— configuration.

In addition to fosetyl-Al, propamocarb-HCl and an insecticide compound B as herein-defined, the composition according to the invention can comprise a further fungicide compound C preferably selected in the list consisting of:
 C1) a compound capable to inhibit the nucleic acid synthesis like benalaxyl, benalaxyl-M, bupirimate, clozylacon, dimethirimol, ethirimol, furalaxyl, hymexazol, mefenoxam, metalaxyl, metalaxyl-M, ofurace, oxadixyl, oxolinic acid;
 C2) a compound capable to inhibit the mitosis and cell division like benomyl, carbendazim, diethofencarb, ethaboxam, fuberidazole, pencycuron, thiabendazole, thiophanate-methyl, zoxamide;
 C3) a compound capable to inhibit the respiration for example
  as CI-respiration inhibitor like diflumetorim;
  as CII-respiration inhibitor like boscalid, carboxin, fenfuram, flutolanil, furametpyr, furmecyclox, mepronil, oxycarboxin, penthiopyrad, thifluzamide;

as CIII-respiration inhibitor like amisulbrom, azoxystrobin, cyazofamid, dimoxystrobin, enestrobin, famoxadone, fenamidone, fluoxastrobin, kresoxim-methyl, metominostrobin, orysastrobin, picoxystrobin, pyraclostrobin, trifloxystrobin;

C4) a compound capable of to act as an uncoupler like dinocap, fluazinam, meptyldinocap;

C5) a compound capable to inhibit ATP production like fentin acetate, fentin chloride, fentin hydroxide, silthiofam;

C6) a compound capable to inhibit AA and protein biosynthesis like andoprim, blasticidin-S, cyprodinil, kasugamycin, kasugamycin hydrochloride hydrate, mepanipyrim, pyrimethanil;

C7) a compound capable to inhibit the signal transduction like fenpiclonil, fludioxonil, quinoxyfen;

C8) a compound capable to inhibit lipid and membrane synthesis like biphenyl, chlozolinate, edifenphos, etridiazole, iodocarb, iprobenfos, iprodione, isoprothiolane, procymidone, pyrazophos, tolclofos-methyl, vinclozolin;

C9) a compound capable to inhibit ergosterol biosynthesis like aldimorph, azaconazole, bitertanol, bromuconazole, cyproconazole, diclobutrazole, difenoconazole, diniconazole, diniconazole-M, dodemorph, dodemorph acetate, epoxiconazole, etaconazole, fenarimol, fenbuconazole, fenhexamid, fenpropidin, fenpropimorph, fluquinconazole, flurprimidol, flusilazole, flutriafol, furconazole, furconazole-cis, hexaconazole, imazalil, imazalil sulfate, imibenconazole, ipconazole, metconazole, myclobutanil, naftifine, nuarimol, oxpoconazole, paclobutrazol, pefurazoate, penconazole, prochloraz, propiconazole, prothioconazole, pyributicarb, pyrifenox, simeconazole, spiroxamine, tebuconazole, terbinafine, tetraconazole, triadimefon, triadimenol, tridemorph, triflumizole, triforine, triticonazole, uniconazole, viniconazole, voriconazole;

C10) a compound capable to inhibit cell wall synthesis like benthiavalicarb, bialaphos, dimethomorph, flumorph, iprovalicarb, mandipropamid, polyoxins, polyoxorim, validamycin A;

C11) a compound capable to inhibit melanine biosynthesis like carpropamid, diclocymet, fenoxanil, phthalide, pyroquilon, tricyclazole;

C12) a compound capable to induce a host defence like acibenzolar-S-methyl, probenazole, tiadinil;

C13) a compound capable to have a multisite action like Bordeaux mixture, captafol, captan, chlorothalonil, copper naphthenate, copper oxide, copper oxychloride, copper preparations such as copper hydroxide, copper sulphate, dichlofluanid, dithianon, dodine, dodine free base, ferbam, fluorofolpet, folpet, guazatine, guazatine acetate, iminoctadine, iminoctadine albesilate, iminoctadine triacetate, mancopper, mancozeb, maneb, metiram, metiram zinc, oxinecopper, propineb, sulphur and sulphur preparations including calcium polysulphide, thiram, tolylfluanid, zineb, ziram;

C14) benthiazole, bethoxazin, capsimycin, carvone, chinomethionat, cufraneb, cyflufenamid, cymoxanil, dazomet, debacarb, dichlorophen, diclomezine, dicloran, difenzoquat, difenzoquat methylsulphate, diphenylamine, ethaboxam, ferimzone, flumetover, flusulfamide, fluopicolide, fluopyram also known as N-{2-[3-chloro-5-(trifluoromethyl)pyridin-2-yl]ethyl}-2-(trifluoromethyl)benzamide, fluoroimide, hexachlorobenzene, 8-hydroxyquinoline sulfate, irumamycin, isotianil, methasulphocarb, metrafenone, methyl isothiocyanate, mildiomycin, natamycin, nickel dimethyldithiocarbamate, nitrothal-isopropyl, octhilinone, oxamocarb, oxyfenthiin, pentachlorophenol and salts, 2-phenylphenol and salts, phosphorous acid and its salts, piperalin, propamocarb-fosetylate also known as dimethyl-[3-(propoxycarbonylamino)propyl]ammonium-β-ethylphosphonate, propanosine-sodium, proquinazid, pyribencarb, pyrroInitrine, quintozene, tecloftalam, tecnazene, triazoxide, trichlamide, valiphenal, zarilamid and 2,3,5,6-tetrachloro-4-(methylsulfonyl)-pyridine, N-(4-chloro-2-nitrophenyl)-N-ethyl-4-methyl-benzenesulfonamide, 2-amino-4-methyl-N-phenyl-5-thiazolecarboxamide, 2-chloro-N-(2,3-dihydro-1,1,3-trimethyl-1H-inden-4-yl)-3-pyridincarboxamide, 3-[5-(4-chlorophenyl)-2,3-dimethylisoxazolidin-3-yl]pyridine, cis-1-(4-chlorophenyl)-2-(1H-1,2,4-triazole-1-yl)-cycloheptanol, methyl 1-(2,3-dihydro-2,2-dimethyl-1H-inden-1-yl)-1H-imidazole-5-carboxylate, 3,4,5-trichloro-2,6-pyridinedicarbonitrile, methyl-2-[[[cyclopropyl[(4-methoxyphenyl)imino]methyl]thio]methyl]-.alpha.-(methoxymethylene)-benzeneacetate, 4-chloro-alpha-propynyloxy-N-[2-[3-methoxy-4-(2-propynyloxy)phenyl]ethyl]-benzeneacetamide, (2S)—N-[2-[4-[[3-(4-chlorophenyl)-2-propynyl]oxy]-3-methoxyphenyl]ethyl]-3-methyl-2-[(methylsulfonyl)amino]-butanamide, 5-chloro-7-(4-methylpiperidin-1-yl)-6-(2,4,6-trifluorophenyl)[1,2,4]triazolo[1,5-a]pyrimidine, 5-chloro-6-(2,4,6-trifluorophenyl)-N-[(1R)-1,2,2-trimethylpropyl][1,2,4]triazolo[1,5-a]pyrimidin-7-amine, 5-chloro-N-[(1R)-1,2-dimethylpropyl]-6-(2,4,6-trifluorophenyl)[1,2,4]triazolo[1,5-a]pyrimidin-7-amine, N-[1-(5-bromo-3-chloropyridin-2-yl)ethyl]-2,4-dichloronicotinamide, N-(5-bromo-3-chloropyridin-2-yl)methyl-2,4-dichloronicotinamide, 2-butoxy-6-iodo-3-propyl-benzopyranon-4-one, N-{(Z)-[(cyclopropylmethoxy)imino][6-(difluoromethoxy)-2,3-difluorophenyl]methyl}-2-phenylacetamide, N-{2-[1,1'-bi(cyclopropyl)-2-yl]phenyl}-3-(difluoromethyl)-1-methyl-1H-pyrazole-4-carboxamide, N-ethyl-N-methyl-N'-{2-methyl-5-(trifluoromethyl)-4-[3-(trimethylsilyl)propoxy]phenyl}imidoformamide, N-ethyl-N-methyl-N'-{2-methyl-5-(difluoromethyl)-4-[3-(trimethylsilyl)propoxy]phenyl}imidoformamide, N-(3-ethyl-3,5,5-trimethyl-cyclohexyl)-3-formylamino-2-hydroxy-benzamide, N-(4-chlorobenzyl)-3-[3-methoxy-4-(prop-2-yn-1-yloxy)phenyl]propanamide, N-[(4-chlorophenyl)(cyano)methyl]-3-[3-methoxy-4-(prop-2-yn-1-yloxy)phenyl]propanamide, 2-[[[[1-[3(1-Fluoro-2-phenylethyl)oxy]phenyl]ethylidene]amino]oxy]methyl]-alpha-(methoxyimino)-N-methyl-alphaE-benzeneacetamide, N-(3',4'-dichloro-5-fluorobiphenyl-2-yl)-3-(difluoromethyl)-1-methyl-1H-pyrazole-4-carboxamide, 2-(2-{[6-(3-chloro-2-methylphenoxy)-5-fluoropyrimidin-4-yl]oxy}phenyl)-2-(methoxyimino)-N-methylacetamide, 1-[(4-methoxyphenoxy)methyl]-2,2-dimethylpropyl-1H-imidazole-1-carboxylic acid, O-[1-[(4-methoxyphenoxy)methyl]-2,2-dimethylpropyl]-1H-imidazole-1-carbothioic acid, a dipetic mixture of methyl-[S—(R,S)]-[3-(N-isopropoxycarbonylvalinyl)-amino]-3-(4-chloro-phenyl)propanoate, methyl-(2-chloro-5-{(1E)-N-[(6-methylpyridin-2-yl)methoxy]-ethanimidoyl}benzyl) carbamate, 4-chloro-alpha-methoxy-N-[2-[3-methoxy-4-(2-propynyloxy)phenyl]ethyl]-benzeneacetamide, 3,4-dichloro-N-(2-cyanophenyl)isothiazole-5-carboxamide, N-[2-(1,3-dimethyl-butyl)-phenyl]-5-fluoro-1,3-dimethyl-1H-pyrazole-4-carboxamide.

Most preferred compounds C in the composition according to the invention can be selected in the list consisting of benalaxyl, benalaxyl-M, benthiavalicarb, carboxin, chlorothalonil, cyazofamid, cymoxanil, dimetomorph, fluazinam, fludioxonil, fluoxastrobin, fluquinconazole, flutriafol, hexaconazole, hymexazol, ipconazole, mancozeb, mandipropamid, maneb, mefenoxam, metalaxyl, metiram, penconazole, penthiopyrad, phosphorous acid, propamocarb-fosetylate, propineb, prothioconazole, tebuconazole, thiram, triadimenol, trifloxystrobin, triticonazole and N-[2-(1,3-dimethyl-butyl)-phenyl]-5-fluoro-1,3-dimethyl-1H-pyrazole-4-carboxamide.

The composition according to the invention preferably comprises

A) fosetyl-Al and propamocarb-HCl;

B) an insecticide compound selected in the list consisting of abamectin, aldicarb, beta-cyfluthrin, chlorpyrifos-E, clothianidin, cyromazine, deltamethrin, diflubenzuron, emamectin-benzoate, fipronil, gamma-cyhalothrin, imidacloprid, L-cyhalothrin, methiocarb, pymetrozine, rynaxapyr, spinosad, spirodiclofen, spiromesifen, spirotetramate, tebufenozide, tebufenpyrad, tefluthrin, thiamethoxam, thiodicarb, imidaclothiz, (2E)-1-[(2-chloro-1,3-thiazol-5-yl)methyl]-3,5-dimethyl-N-nitro-1,3,5-triazinan-2-imine and C) a further fungicide compound selected in the list consisting of benalaxyl, benalaxyl-M, benthiavalicarb, carboxin, chlorothalonil, cyazofamid, cymoxanil, dimetomorph, fluazinam, fludioxonil, fluoxastrobin, fluquinconazole, flutriafol, hexaconazole, hymexazol, ipconazole, mancozeb, mandipropamid, maneb, mefenoxam, metalaxyl, metiram, penconazole, penthiopyrad, phosphorous acid, propamocarb-fosetylate, propineb, prothioconazole, tebuconazole, thiram, triadimenol, trifloxystrobin, triticonazole and N-[2-(1,3-dimethyl-butyl)-phenyl]-5-fluoro-1,3-dimethyl-1H-pyrazole-4-carboxamide.

For the composition according to the invention the A/B/C weight ratio preferably ranges from 1/100/100 to 1/0.01/0.01; more preferably from 1/80/80 to 1/0.05/0.05; even more preferably from 1/50/100 to 1/1.5/2.5; still even more preferably from 1/12/25 to 1/6/12.

According to another aspect of the present invention, in the pesticide composition according to the invention, the compound ratio A/B/C can be advantageously selected so as to produce a synergistic effect. The term synergistic effect is understood to mean in particular that defined by Colby in an article entitled "Calculation of the synergistic and antagonistic responses of herbicide combinations" Weeds, (1967), 15, pages 20-22.

The latter article mentions the formula:

$$E = X + Y + Z - \frac{XYZ}{100}$$

wherein E represents the expected percentage of inhibition of the pest for the combination of the three compounds at defined doses (for example equal to x, y and z respectively), X is the percentage of inhibition observed for the pest by compounds A1 and A2 at defined doses (equal to x=x1+x2), Y is the percentage of inhibition observed for the pest by compound B at a defined dose (equal to y) and Z is the percentage of inhibition observed for the pest by compound C at a defined dose (equal to z). When the percentage of inhibition observed for the combination is greater than E, there is a synergistic effect.

The term "synergistic effect" also means the effect defined by application of the Tammes method, "Isoboles, a graphic representation of synergism in pesticides", Netherlands Journal of Plant Pathology, 70 (1964), pages 73-80.

The pesticide composition according to the invention may comprise from 0.00001 to 100%, preferably from 0.001 to 80%, of active compounds, whether these compounds are combined, or whether they are in the form of two or more active ingredients used separately.

More generally, the pesticide composition according to the invention may eventually also comprise one or more other active substances selected from fungicide, herbicide, insecticide or plant growth regulator active compounds.

In addition to these additional active agents, the pesticide composition according to the invention may also comprise any other adjuvants or auxiliary agent useful in plant protection formulations such as, for example, an agriculturally suitable inert carrier and optionally an agriculturally suitable surfactant.

For its practical use, the pesticide composition according to the invention can be used alone or in formulations containing one or the other of the active ingredients or alternatively both of them together, in combination or association with one or more other compatible components which are, for example, solid or liquid fillers or diluents, adjuvants, surfactants or equivalents, which are suitable for the desired use and which are acceptable for uses in agriculture. The formulations can be of any type known in the sector that is suitable for application onto all types of cultures or crops. These formulations, which can be prepared in any manner known by the skilled person, also form part of the invention.

The formulations may also contain ingredients of other types, such as protective colloids, adhesives, thickeners, thixotropic agents, penetrating agents, oils for spraying, stabilisers, preserving agents (in particular mould-proofing or biocide agents), sequestering or chelating agents or the like. More generally, the compounds used in the invention can be combined with any solid or liquid additives corresponding to the usual formulation techniques.

The term "filler" means an organic or inorganic, natural or synthetic component with which the active components are combined to facilitate its application, for example, onto the plants, the seeds or the soil. This filler is consequently generally inert and it must be acceptable (for example acceptable for agronomic uses, in particular for treating plants).

The filler can be solid, for example clays, natural or synthetic silicates, silica, resins, waxes, solid fertilizers (for example ammonium salts), natural soil minerals, such as kaolins, clays, talc, lime, quartz, attapulgite, montmorillonite, bentonite or diatomaceous earths, or synthetic minerals, such as silica, alumina or silicates, in particular aluminium or magnesium silicates. The solid fillers which are suitable for granules are as follows: natural, crushed or broken rocks, such as calcite, marble, pumice, sepiolite and dolomite; synthetic granules of inorganic or organic flours; granules of organic material such as sawdust, coconut shell, corn ear or envelope, or tobacco stem; kieselguhr, tricalcium phosphate, powdered cork or adsorbent carbon black; water-soluble polymers, resins, waxes; or solid fertilizers. Such composition may, if so desired, contain one or more compatible agents such as wetting agents, dispersing agents, emulsifiers or colourings which, when they are solid, may also act as diluents.

The fillers may also be liquid, for example: water, alcohols, in particular butanol or glycol, as well as ethers or esters thereof, in particular methyl glycol acetate; ketones, in particular acetone, cyclohexanone, methyl ethyl ketone, methyl isobutyl ketone or isophorone; petroleum fractions such as paraffinic or aromatic hydrocarbons, in particular xylenes or alkylnaphthalenes; mineral or plant oils; aliphatic chlorohydrocarbons, in particular trichloroethane or methylene chloride; aromatic chlorohydrocarbons, in particular chlorobenzenes; water-soluble or highly polar solvents such as dimethylformamide, dimethyl sulphoxide, N,N-dimethyl-acetamide or N-methylpyrrolidone; N-octylpyrrolidone, liquefied gases; or the like, whether they are taken separately or as a mixture.

The surfactant can be an emulsifier, a dispersing agent or a wetting agent, of ionic or nonionic type or a mixture of these surfactants. Among those surfactants there are used, for example, polyacrylic acid salts, lignosulphonic acid salts, phenolsulphonic or naphthalenesulphonic acid salts, polycondensates of ethylene oxide with fatty alcohols or fatty acids or fatty esters or fatty amines, substituted phenols (in particular alkylphenols or arylphenols), ester-salts of sulphosuccinic acid, taurine derivatives (in particular alkyl taurates), phosphoric esters of alcohols or of polycondensates of ethylene oxide with phenols, fatty acid esters with polyols, or sulphate, sulphonate or phosphate functional derivatives of the compounds described above. The presence of at least one surfactant is generally essential when the active ingredients and/or the inert filler are insoluble or only sparingly soluble in water and when the filler for the said composition to be applied is water.

The formulations may also contain other additives such as adhesives or dyes. Adhesives such as carboxymethylcellulose or natural or synthetic polymers in the form of powders, granules or matrices, such as gum arabic, latex, polyvinylpyrrolidone, polyvinyl alcohol or polyvinyl acetate, natural phospholipids, such as cephalins or lecithins, or synthetic phospholipids can be used in the formulations. It is possible to use colourings such as inorganic pigments, such as, for example: iron oxides, titanium oxides, Prussian blue; organic colouring stuffs, such as those of the alizarin, azo or metal phthalocyanin type; or of trace elements such as iron, manganese, boron, copper, cobalt, molybdenum or zinc salts.

The form of the pesticide composition according to the invention can be selected in a large number of formulations, such as aerosol dispenser; suspension of capsules; cold fogging concentrate; dustable powder; emulsifiable concentrate; aqueous/aqueous type emulsion; oil/inverse type emulsion; encapsulated granule; fine granule; suspension concentrate for seed treatment; compressed gas; gas generating product; granule; hot fogging concentrate; macrogranule; microgranule; oil-dispersible powder; oil miscible suspension concentrate; oil-miscible liquid; paste; plant rodlet; powder for dry seed treatment; seeds coated with a pesticide; smoke maydle; smoke cartridge; smoke generator; smoke pellet; smoke rodlet; smoke tablet; smoke tin; soluble concentrate; soluble powder; solution for seed treatment; suspension concentrate (=flowable concentrate); ultra low volume liquid; ultra low volume suspension; vapour releasing product; water-dispersible granules or tablets; water dispersible powder for slurry treatment; water-soluble granules or tablets; water-soluble powder for seed treatment; wettable powder.

The pesticide composition according to the present invention covers not only the compositions which are ready to be applied to the crop by means of a suitable device, such as a spraying device, but also the commercial concentrated composition which have to be diluted before application to the crop.

The pesticide composition herein described is used in general for application to growing plants, or to sites where crops are grown or intended to grow, or for the treatment, coating or film-coating of seeds.

According to the present invention, seeds may comprise any propagation materials, like for example seeds, fruit, tubers, grains, roots, rhizomes, parts of plants.

The pesticide composition according to the invention may also be applied to the vegetation and in particular to the leaves infested or capable of being infested with the phytopathogenic fungi or damaged by insects. Another method of applying the pesticide composition according to the invention is to add a formulation containing the active ingredients to the irrigation water.

According to another object of the present invention, there is provided a method for controlling the phytopathogenic fungi or damaging insects of plants, crops or seeds, characterized in that an agronomically effective and substantially non-phytotoxic quantity of a pesticide composition according to the invention is applied as seed treatment, foliar application, stem application, drench or drip application (chemigation) to the seed, the plant or to the fruit of the plant or to soil or to inert substrate (e.g. inorganic substrates like sand, rockwool, glasswool; expanded minerals like perlite, vermiculite, zeolite or expanded clay), Pumice, Pyroclastic materials or stuff, synthetic organic substrates (e.g. polyurethane), organic substrates (e.g. peat, composts, tree waste products like coir, wood fibre or chips, tree bark) or to a liquid substrate (e.g. floating hydroponic systems, Nutrient Film Technique, Aeroponics) wherein the plant is growing or in which it is desired to grow.

The expression "are applied to the plants to be treated" is understood to mean, for the purposes of the present invention, that the pesticide composition which is the subject of the invention can be applied by means of various methods of treatment such as:
  spraying onto the aerial parts of the said plants a liquid comprising one of the said compositions,
  dusting, the incorporation into the soil of granules or powders, spraying, around the said plants, and in the case of trees injection or daubing,
  coating or film-coating the seeds of the said plants with the aid of a plant-protection mixture comprising one of the said compositions.

The method according to the invention may either be a curing, preventing or eradicating method.

In this method, a composition used can be prepared beforehand by mixing the two or more active compounds according to the invention.

According to an alternative of such a method, it is also possible to apply simultaneously, successively or separately compounds (A1 and A2) and (B) and optionally (C) so as to have the conjugated (A1 and A2)/(B) (optionally (C)) effects, of distinct compositions each containing one of the two or three active ingredients (A1 and A2) or (B), optionally (C). Such a method can be extended to the further application of compound (C).

The dose of active compound usually applied in the method of treatment according to the invention is generally and advantageously
  for foliar treatments: from 0.1 to 10,000 g/ha, preferably from 10 to 1,000 g/ha, more preferably from 50 to 300 g/ha; in case of drench or drip application, the dose can even be reduced, especially while using inert substrates like rockwool or perlite;
  for seed treatment: from 2 to 200 g per 100 kilogram of seed, preferably from 3 to 150 g per 100 kilogram of seed;
  for soil treatment: from 0.1 to 10,000 g/ha, preferably from 1 to 5,000 g/ha.

The doses herein indicated are given as illustrative examples of the method according to the invention. A person skilled in the art will know how to adapt the application doses, notably according to the nature of the plant or crop to be treated.

Under specific conditions, for example according to the nature of the phytopathogenic fungus to be treated or insect to control, a lower dose may offer adequate protection. Certain climatic conditions, resistance or other factors like the nature of the phytopathogenic fungi or damaging insect to be eliminated or the degree of infestation, for example, of the plants with these fungi, may require higher doses of combined active ingredients.

The optimum dose usually depends on several factors, for example on the type of phytopathogenic fungus to be treated or insect to control, on the type or level of development of the infested plant, on the density of vegetation, or alternatively on the method of application.

Without it being limiting, the crop treated with the pesticide composition or combination according to the invention is, for example, grapevine, but this could be cereals, vegetables, lucerne, soybean, market garden crops, turf, wood, tree or horticultural plants.

The method of treatment according to the invention may also be useful to treat propagation material such as tubers or rhizomes, but also seeds, seedlings or seedlings pricking out and plants or plants pricking out. This method of treatment may also be useful to treat roots. The method of treatment according to the invention may also be useful to treat the over-ground parts of the plant such as trunks, stems or stalks, leaves, flowers and fruit of the concerned plant.

Among the plants that can be protected by the method according to the invention, mention can be made of cotton; flax; vine; fruit or vegetable crops such as Rosaceae sp. (for instance pip fruit such as apples and pears, but also stone fruit such as apricots, almonds and peaches), Ribesioidae sp., Juglandaceae sp., Betulaceae sp., Anacardiaceae sp., Fagaceae sp., Moraceae sp., Oleaceae sp., Actimidaceae sp., Lauraceae sp., Musaceae sp. (for instance banana trees and plantins), Rubiaceae sp., Theaceae sp., Sterculiceae sp., Rutaceae sp. (for instance lemons, oranges and grapefruit); Solanaceae sp. (for instance tomatoes), Liliaceae sp., Asteraceae sp. (for instance lettuces), Umbelliferae sp., Cruciferae sp., Chenopodiaceae sp., Cucurbitaceae sp., Papilionaceae sp. (for instance peas), Rosaceae sp. (for instance strawberries); major crops such as Graminae sp. (for instance maize, lawn or cereals such as wheat, rice, barley and triticale), Asteraceae sp. (for instance sunflower), Cruciferae sp. (for instance colza), Fabacae sp. (for instance peanuts), Papilionaceae sp. (for instance soybean), Solanaceae sp. (for instance potatoes), Chenopodiaceae sp. (for instance beetroots); horticultural and forest crops; as well as genetically modified homologues of these crops.

The composition according to the invention may also be used in the treatment of genetically modified organisms with the compounds according to the invention or the agrochemical compositions according to the invention. Genetically modified plants are plants into genome of which a heterologous gene encoding a protein of interest has been stably integrated. The expression "heterologous gene encoding a protein of interest" essentially means genes which give the transformed plant new agronomic properties, or genes for improving the agronomic quality of the modified plant.

The composition according to the invention may also be used against fungal diseases liable to grow on or inside timber. The term "timber" means all types of species of wood, and all types of working of this wood intended for construction, for example solid wood, high-density wood, laminated wood, and plywood. The method for treating timber according to the invention mainly consists in contacting one or more compounds according to the invention, or a composition according to the invention; this includes for example direct application, spraying, dipping, injection or any other suitable means.

Among the diseases of plants or crops that can be controlled by the method according to the invention, mention can be made of:

Powdery mildew diseases such as:

*Blumeria* diseases, caused for example by *Blumeria graminis*;

*Podosphaera* diseases, caused for example by *Podosphaera leucotricha*;

*Sphaerotheca* diseases, caused for example by *Sphaerotheca fuliginea*;

*Uncinula* diseases, caused for example by *Uncinula necator*;

Rust diseases such as:

*Gymnosporangium* diseases, caused for example by *Gymnosporangium sabinae*;

*Hemileia* diseases, caused for example by *Hemileia vastatrix*;

*Phakopsora* diseases, caused for example by *Phakopsora pachyrhizi* or *Phakopsora meibomiae*;

*Puccinia* diseases, caused for example by *Puccinia recondite*;

*Uromyces* diseases, caused for example by *Uromyces appendiculatus*;

Oomycete diseases such as:

*Bremia* diseases, caused for example by *Bremia lactucae*;

*Peronospora* diseases, caused for example by *Peronospora pisi* or *P. brassicae*;

*Phytophthora* diseases, caused for example by *Phytophthora infestans*;

*Plasmopara* diseases, caused for example by *Plasmopara viticola*;

*Pseudoperonospora* diseases, caused for example by *Pseudoperonospora humuli* or *Pseudoperonospora cubensis*;

*Pythium* diseases, caused for example by *Pythium ultimum*;

Leafspot, leaf blotch and leaf blight diseases such as:

*Alternaria* diseases, caused for example by *Alternaria solani*;

*Cercospora* diseases, caused for example by *Cercospora beticola*;

*Cladiosporum* diseases, caused for example by *Cladiosporium cucumerinum*;

*Cochliobolus* diseases, caused for example by *Cochliobolus sativus*;

*Colletotrichum* diseases, caused for example by *Colletotrichum lindemuthanium*;

*Cycloconium* diseases, caused for example by *Cycloconium oleaginum*;

*Diaporthe* diseases, caused for example by *Diaporthe citri*;

*Elsinoe* diseases, caused for example by *Elsinoe fawcettii*;

*Gloeosporium* diseases, caused for example by *Gloeosporium laeticolor*;

*Glomerella* diseases, caused for example by *Glomerella cingulata*;

*Guignardia* diseases, caused for example by *Guignardia bidwelli*;

*Leptosphaeria* diseases, caused for example by *Leptosphaeria maculans*; *Leptosphaeria nodorum*;

*Magnaporthe* diseases, caused for example by *Magnaporthe grisea*;

*Mycosphaerella* diseases, caused for example by *Mycosphaerella graminicola*;

*Mycosphaerella arachidicola*; *Mycosphaerella Riensis*;

*Phaeosphaeria* diseases, caused for example by *Phaeosphaeria nodorum*;

*Pyrenophora* diseases, caused for example by *Pyrenophora teres*;

*Ramularia* diseases, caused for example by *Ramularia collo-cygni*;

*Rhynchosporium* diseases, caused for example by *Rhynchosporium secalis*;

*Septoria* diseases, caused for example by *Septoria apii* or *Septoria lycopercisi*;

*Typhula* diseases, caused for example by *Typhula incarnate*;

*Venturia* diseases, caused for example by *Venturia inaequalis*;

Root and stem diseases such as:

*Corticium* diseases, caused for example by *Corticium graminearum*;

*Fusarium* diseases, caused for example by *Fusarium oxysporum*;

*Gaeumannomyces* diseases, caused for example by *Gaeumannomyces graminis*;

*Rhizoctonia* diseases, caused for example by *Rhizoctonia solani*;

*Tapesia* diseases, caused for example by *Tapesia acuformis*;

*Thielaviopsis* diseases, caused for example by *Thielaviopsis basicola*;

Ear and panicle diseases such as:

*Alternaria* diseases, caused for example by *Alternaria* spp.;

*Aspergillus* diseases, caused for example by *Aspergillus flavus*;

*Cladosporium* diseases, caused for example by *Cladosporium* spp.;

*Claviceps* diseases, caused for example by *Claviceps purpurea*;

*Fusarium* diseases, caused for example by *Fusarium culmorum*;

*Gibberella* diseases, caused for example by *Gibberella zeae*;

*Monographella* diseases, caused for example by *Monographella nivalis*;

Smut and bunt diseases such as:

*Sphacelotheca* diseases, caused for example by *Sphacelotheca reiliana*;

*Tilletia* diseases, caused for example by *Tilletia caries*;

*Urocystis* diseases, caused for example by *Urocystis occulta*;

*Ustilago* diseases, caused for example by *Ustilago nuda*;

Fruit rot and mould diseases such as:

*Aspergillus* diseases, caused for example by *Aspergillus flavus*;

*Botrytis* diseases, caused for example by *Botrytis cinerea*;

*Penicillium* diseases, caused for example by *Penicillium expansum*;

*Sclerotinia* diseases, caused for example by *Sclerotinia sclerotiorum*;

*Verticilium* diseases, caused for example by *Verticilium alboatrum*;

Seed and soilborne decay, mould, wilt, rot and damping-off diseases:

*Fusarium* diseases, caused for example by *Fusarium culmorum*;

*Phytophthora* diseases, caused for example by *Phytophthora cactorum*;

*Pythium* diseases, caused for example by *Pythium ultimum*;

*Rhizoctonia* diseases, caused for example by *Rhizoctonia solani*;

*Sclerotium* diseases, caused for example by *Sclerotium rolfsii*;

*Microdochium* diseases, caused for example by *Microdochium nivale*;

Canker, broom and dieback diseases such as:

*Nectria* diseases, caused for example by *Nectria galligena*;

Blight diseases such as:

*Monilinia* diseases, caused for example by *Monilinia laxa*;

Leaf blister or leaf curl diseases such as:

*Taphrina* diseases, caused for example by *Taphrina deformans*;

Decline diseases of wooden plants such as:

Esca diseases, caused for example by *Phaemoniella clamydospora*;

*Eutypa* dyeback, caused for example by *Eutypa lata*;

Dutch elm disease, caused for example by *Ceratocystsc ulmi*;

Diseases of flowers and Seeds such as:

*Botrytis* diseases, caused for example by *Botrytis cinerea*;

Diseases of tubers such as:

*Rhizoctonia* diseases, caused for example by *Rhizoctonia solani*

*Helminthosporium* diseases, caused for example by *Helminthosporium solani*.

The damaging insects of crops which can be controlled at any development stage by using the pesticide composition according to the invention include:

pests from the order of Isopoda for example *Oniscus asellus, Armadillidium vulgare, Porcellio scaber*;

pests from the order of Diplopoda for example *Blaniulus guttulatus*;

pests from the order of Chilopoda for example *Geophilus carpophagus, Scutigera* spp.;

pests from the order of Symphyla for example *Scutigerella immaculata*;

pests from the order of Thysanura for example *Lepisma saccharina*;

pests from the order of Collembola for example *Onychiurus armatus*;

pests from the order of Orthoptera for example *Acheta domesticus, Gryllotalpa* spp., *Locusta migratoria migratorioides, Melanoplus* spp., *Schistocerca gregaria*;

pests from the order of Blattaria for example *Blatta orientalis, Periplaneta americana, Leucophaea maderae, Blattella germanica*;

pests from the order of Dermaptera for example *Forficula auricularia*;

pests from the order of Isoptera for example *Reticulitermes* spp.;

pests from the order of Phthiraptera for example *Pediculus humanus corporis, Haematopinus* spp., *Linognathus* spp., *Trichodectes* spp., *Damalinia* spp.;

pests from the order of Thysanoptera for example *Hercinothrips femoralis, Thrips tabaci, Thrips palmi, Frankliniella accidentalis*;

pests from the order of Heteroptera for example *Eurygaster* spp., *Dysdercus intermedius, Piesma quadrata, Cimex lectularius, Rhodnius prolixus, Triatoma* spp;

pests from the order of Homoptera for example *Aleurodes brassicae, Bemisia tabaci, Trialeurodes vaporariorum, Aphis gossypii, Brevicoryne brassicae, Cryptomyzus ribis, Aphis fabae, Aphis pomi, Eriosoma lanigerum, Hyalopterus arundinis, Phylloxera vastatrix, Pemphigus* spp., *Macrosiphum avenae, Myzus* spp., *Phorodon humuli, Rhopalosiphum padi, Empoasca* spp., *Euscelis bilobatus, Nephotettix cincticeps, Lecanium corni, Sais-* setia oleae, Laodelphax striatellus, Nilaparvata lugens, Aonidiella aurantii, Aspidiotus hederae, Pseudococcus spp., Psylla spp;

pests from the order of Lepidoptera for example Pectinophora gossypiella, Bupalus piniarius, Chematobia brumata, Lithocolletis blancardella, Hyponomeuta padella, Plutella xylostella, Malacosoma neustria, Euproctis chrysorrhoea, Lymantria spp., Bucculatrix thurberiella, Phyllocnistis citrella, Agrotis spp., Euxoa spp., Feltia spp., Earias insulana, Heliothis spp., Mamestra brassicae, Panolis flammea, Spodoptera spp., Trichoplusia ni, Carpocapsa pomonella, Pieris spp., Chilo spp., Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima, Tortrix viridana, Cnaphalocerus spp., Oulema oryzae;

pests from the order of Coleoptera for example Anobium punctatum, Rhizopertha dominica, Bruchidius obtectus, Acanthoscelides obtectus, Hylotrupes bajulus, Agelastica alni, Leptinotarsa decemlineata, Phaedon cochleariae, Diabrotica spp., Psylliodes chrysocephala, Epilachna varivestis, Atomaria spp., Oryzaephilus surinamensis, Anthonomus spp., Sitophilus spp., Otiorrhynchus sulcatus, Cosmopolites sordidus, Ceuthorrhynchus assimilis, Hypera postica, Dermestes spp., Trogoderma spp., Anthrenus spp., Attagenus spp., Lyctus spp., Meligethes aeneus, Ptinus spp., Niptus hololeucus, Gibbium psylloides, Tribolium spp., Tenebrio molitor, Agriotes spp., Conoderus spp., Melolontha melolontha, Amphimallon solstitialis, Costelytra zealandica, Lissorhoptrus oryzophilus;

pests from the order of Hymenoptera for example Diprion spp., Hoplocampa spp., Lasius spp., Monomorium pharaonis, Vespa spp;

pests from the order of Diptera for example Aedes spp., Anopheles spp., Culex spp., Drosophila melanogaster, Musca spp., Fannia spp., Calliphora erythrocephala, Lucilia spp., Chrysomyia spp., Cuterebra spp., Gastrophilus spp., Hyppobosca spp., Stomoxys spp., Oestrus spp., Hypoderma spp., Tabanus spp., Tannia spp., Bibio hortulanus, Oscinella frit, Phorbia spp., Pegomyia hyoscyami, Ceratitis capitata, Dacus oleae, Tipula paludosa, Hylemyia spp., Liriomyza spp.;

pests from the order of Siphonaptera for example Xenopsylla cheopis, Ceratophyllus spp.;

pests from the class of Arachnida for example Scorpio maurus, Latrodectus mactans, Acarus siro, Argas spp., Ornithodoros spp., Dermanyssus gallinae, Eriophyes ribis, Phyllocoptruta oleivora, Boophilus spp., Rhipicephalus spp., Amblyomma spp., Hyalomma spp., Ixodes spp., Psoroptes spp., Chorioptes spp., Sarcoptes spp., Tarsonemus spp., Bryobia praetiosa, Panonychus spp., Tetranychus spp., Hemitarsonemus spp., Brevipalpus spp;

the plant-parasitic neamnotes such as Pratylenchus spp., Radopholus similis, Ditylenchus dipsaci, Tylenchulus semipenetrans, Heterodera spp., Globodera spp., Meloidogyne spp., Aphelenchoides spp., Longidorus spp., Xiphinema spp., Trichodorus spp., Bursaphelenchus spp.

As a further aspect, the present invention provides a product comprising compounds (A1 and A2) and a compound (B) and optionally a compound (C), as herein defined, as a combined preparation for simultaneous, separate or sequential use in controlling the phytopathogenic fungi or damaging insects of plants, crops or seeds at a site.

The pesticide composition according to the invention can be prepared immediately before use by using a kit-of-parts for controlling, curatively or preventively, the phytopathogenic fungi of crops, such a kit-of-parts may comprise at least compounds (A1 and A2) and at least one compound (B) and optionally compound (C) intended to be combined or used simultaneously, separately or sequentially in controlling the phytopathogenic fungi of crops at a site.

It is therefore a pack in which the user finds all the ingredients for preparing the fungicide formulation which they wish to apply to the crops. These ingredients, which comprise in particular the active agents (A1 and A2) and (B) and optionally compound (C) and which are packaged separately, are provided in the form of a powder or in the form of a liquid which is concentrated to a greater or lesser degree. The user simply has to mix in the prescribed doses and to add the quantities of liquid, for example of water, necessary to obtain a formulation which is ready to use and which can be applied to the crops.

The present invention can be illustrated by the following and non-limitative examples.

Efficacy Example A

Spodoptera Exigua Test

| Solvent: | 7 parts by weight of dimethylformamide |
|---|---|
| Emulsifier: | 2 parts by weight of alkylaryl polyglycolether |

To produce a suitable preparation of active compound, 1 part by weight of active compound is mixed with the stated amount of solvent and emulsifier, and the concentrate is diluted with emulsifier-containing water to the desired concentration.

Cabbage leaves (Brassica oleracea) are treated by being dipped into the preparation of the active compound at the desired concentration and are infested with larvae of the beet army worm (Spodoptera exigua) as long as the leaves are still moist.

After a period of time of 4 days, the mortality is determined. 100% means that all the caterpillars have been killed; 0% means that none of the caterpillars have been killed.

According to the present application in this test e.g. the following combination shows a synergistic effect in comparison to the single compounds. The results are presented in table 1.

TABLE 1

| | Rate of application of active compound (ppm) | Efficacy (%) | Expected value according to Colby formula (%) |
|---|---|---|---|
| propamocarb-HCl | 200 | 0 | / |
| fosetyl-Al | 200 | 0 | / |
| thiamethoxam | 20 | 0 | / |
| propamocarb-HCl + fosetyl-Al + thiamethoxam | 200 + 200 + 20 | 20 | 0 |

Efficacy Example B

*Spodoptera Frugiperda* Test

| Solvent: | 7 parts by weight of dimethylformamide |
|---|---|
| Emulsifier: | 2 parts by weight of alkylaryl polyglycolether |

To produce a suitable preparation of active compound, 1 part by weight of active compound is mixed with the stated amount of solvent and emulsifier, and the concentrate is diluted with emulsifier-containing water to the desired concentration.

Cabbage leaves (*Brassica oleracea*) are treated by being dipped into the preparation of the active compound at the desired concentration and are infested with larvae of the fall army worm (*Spodoptera frugiperda*) as long as the leaves are still moist.

After a period of time of 4 days, the mortality is determined. 100% means that all the caterpillars have been killed; 0% means that none of the caterpillars have been killed.

According to the present application in this test e.g. the following combination shows a synergistic effect in comparison to the single compounds. The results are presented in table 2.

TABLE 2

|  | Rate of application of active compound (ppm) | Efficacy (%) | Expected value according to Colby formula (%) |
|---|---|---|---|
| propamocarb-HCl | 200 | 10 | / |
| fosetyl-Al | 200 | 0 | / |
| clothianidin | 4 | 50 | / |
| thiacloprid | 20 | 0 | / |
| propamocarb-HCl + fosetyl-Al + clothianidin | 200 + 200 + 4 | 80 | 55 |
| propamocarb-HCl + fosetyl-Al + thiacloprid | 200 + 200 + 20 | 60 | 10 |

Efficacy Example C

*Plutella Xylostella* Test

| Solvent: | 7 parts by weight of dimethylformamide |
|---|---|
| Emulsifier: | 2 parts by weight of alkylaryl polyglycolether |

To produce a suitable preparation of active compound, 1 part by weight of active compound is mixed with the stated amount of solvent and emulsifier, and the concentrate is diluted with emulsifier-containing water to the desired concentration.

Cabbage leaves (*Brassica oleracea*) are treated by being dipped into the preparation of the active compound at the desired concentration and are infested with larvae of the diamond black moth *Plutella xylostella* as long as the leaves are still moist.

After a period of time of 6 days, the mortality is determined. 100% means that all the caterpillars have been killed; 0% means that none of the caterpillars have been killed.

According to the present application in this test e.g. the following combination shows a synergistic effect in comparison to the single compounds. The results are presented in table 3.

TABLE 3

|  | Rate of application of active compound (ppm) | Efficacy (%) | Expected value according to Colby formula (%) |
|---|---|---|---|
| propamocarb-HCl | 200 | 0 | / |
| fosetyl-Al | 200 | 0 | / |
| imidacloprid | 100 | 15 | / |
| fosetyl-Al + thiacloprid | 200 + 200 + 100 | 35 | 15 |

What is claimed is:

1. A composition comprising:
   A) the compounds
      A1) fosetyl-Al
      A2) propamocarb HCl
      in an A1/A2 weight ratio ranging from 1/12 to 12/1, and
   B) an insecticide compound selected from the group consisting of spirotetramate
   in an A/B weight ratio ranging from 1/1,000 to 1,000/1.

2. The composition according to claim 1, wherein the A1/A2 weight ratio ranges from 1/3 to 3/1.

3. The composition according to claim 1, wherein the A1/A2 weight ratio is 1.

4. The composition according to claim 1, wherein the A/B weight ratio ranges from 1/125 to 125/1.

5. The composition according to claim 1 wherein the A/B weight ratio ranges from 1/25 to 25/1.

6. The composition according to claim 1, further comprising:
   C) a further fungicide compound in an A/B/C weight ratio ranging from 1/1,000/1,000 to 1/0.001/0.001.

7. The composition according to claim 6, wherein compound C is selected from the group consisting of benalaxyl, benalaxyl-M, benthiavalicarb, carboxin, chlorothalonil, cyazofamid, cymoxanil, dimetomorph, fluazinam, fludioxonil, fluoxastrobin, fluquinconazole, flutriafol, hexaconazole, hymexazol, ipconazole, mancozeb, mandipropamid, maneb, mefenoxam, metalaxyl, metiram, penconazole, penthiopyrad, phosphorous acid, propamocarb-fosetylate, propineb, prothioconazole, tebuconazole, thiram, triadimenol, trifloxystrobin, triticonazole and N-[2-(1,3-dimethyl-butyl)-phenyl]-5-fluoro-1,3-dimethyl-1H-pyrazole-4-carboxamide.

8. The composition according to claim 6, wherein the A/B/C weight ratio ranges from 1/100/100 to 1/0.01/0.01.

9. The composition according to claim 6, wherein the A/B/C weight ratio ranges from 1/80/80 to 1/0.05/0.05.

10. The composition according to claim 6, wherein the A/B/C weight ratio ranges from 1/50/100 to 1/1.5/2.5.

11. The composition according to claim 6, wherein the A/B/C weight ratio ranges from 1/12/25 to 1/6/12.

12. A method for controlling the phytopathogenic fungi or damaging insects of plants, crops or seeds comprising the application of an agronomically effective and substantially non-phytotoxic quantity of the pesticide composition according to claim 1 as seed treatment, foliar application, stem application, drench or drip application or chemigation to the seed, the plant or to the fruit of the plant or to soil or to inert substrate, Pumice, Pyroclastic materials or stuff, synthetic organic substrates, organic substrates or to a liquid substrate wherein the plant is growing or in which it is desired to grow.

13. A method for controlling the phytopathogenic fungi or damaging insects of plants, crops or seeds comprising the application of an agronomically effective and substantially non-phytotoxic quantity of the pesticide composition according to claim 6 as seed treatment, foliar application, stem application, drench or drip application or chemigation to the seed, the plant or to the fruit of the plant or to soil or to inert substrate, Pumice, Pyroclastic materials or stuff, synthetic organic substrates, organic substrates or to a liquid substrate wherein the plant is growing or in which it is desired to grow.

* * * * *